(12) United States Patent
Watanabe et al.

(10) Patent No.: US 7,094,592 B2
(45) Date of Patent: Aug. 22, 2006

(54) BACILLUS SP. D747 STRAIN, PLANT DISEASE CONTROLLING AGENTS AND INSECT PEST CONTROLLING AGENTS USING THE SAME AND CONTROL METHOD USING THE AGENTS

(75) Inventors: Satoshi Watanabe, Fujinomiya (JP); Jun Toyoshima, Ogasa-gun (JP); Tsutomu Shimizu, Ogasa-gun (JP); Koji Yamaji, Ogasa-gun (JP); Kozo Nagayama, Kakegawa (JP); Hiroyuki Yano, Ogasa-gun (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/495,432

(22) PCT Filed: Nov. 26, 2002

(86) PCT No.: PCT/JP02/12319

§ 371 (c)(1),
(2), (4) Date: May 24, 2004

(87) PCT Pub. No.: WO03/046157

PCT Pub. Date: Jun. 5, 2003

(65) Prior Publication Data

US 2004/0265292 A1 Dec. 30, 2004

(30) Foreign Application Priority Data

Nov. 26, 2001 (JP) ............................. 2001-359222
May 8, 2002 (JP) ............................. 2002-133294

(51) Int. Cl.
*C12N 1/20* (2006.01)
*C12N 1/00* (2006.01)
*A01N 63/00* (2006.01)

(52) U.S. Cl. ............... 435/252.5; 435/243; 424/93.46; 504/117

(58) Field of Classification Search ............. 435/252.5; 424/93.46
See application file for complete search history.

(56) References Cited

U.S. PATENT DOCUMENTS

| | | | | |
|---|---|---|---|---|
| 4,631,857 A | * | 12/1986 | Kase et al. | 43/132.1 |
| 5,378,460 A | * | 1/1995 | Zuckerman et al. | 424/93.461 |
| 5,552,138 A | * | 9/1996 | Handelsman et al. | 424/93.46 |
| 5,589,381 A | * | 12/1996 | Neyra et al. | 435/252.5 |
| 6,103,228 A | * | 8/2000 | Heins et al. | 424/93.462 |

FOREIGN PATENT DOCUMENTS

| | | |
|---|---|---|
| EP | 522836 | 1/1993 |
| JP | 5-51305 | 3/1993 |
| JP | 5-91869 | 4/1993 |
| JP | 6-133763 | 5/1994 |
| WO | WO 98/50422 | 11/1998 |

OTHER PUBLICATIONS

Hoefte, H. et al, "Insecticidal Crystal Proteins of Bacillus Thuringiensis" Microbiological Reviews, American Society for Microbiology, Washington, DC, US, vol. 53, Jun. 1, 1989 (1989-06-01), pp. 242-255.

* cited by examiner

*Primary Examiner*—Irene Marx
*Assistant Examiner*—Lora E Barnhart
(74) *Attorney, Agent, or Firm*—Oblon, Spivak, McClelland, Maier & Neustadt, P.C.

(57) ABSTRACT

The present invention relates to a novel strain of *Bacillus* sp. D747 (deposited as FERM BP-8234) and methods for controlling plant diseases and insect pests, comprising administering cultures of *Bacillus* sp. D747 (including the viable bacteria) or viable bacteria isolated by culturing, on the plant parts such as roots, stems, leaves, seeds, and the like, or in the culture soil.

21 Claims, No Drawings

BACILLUS SP. D747 STRAIN, PLANT DISEASE CONTROLLING AGENTS AND INSECT PEST CONTROLLING AGENTS USING THE SAME AND CONTROL METHOD USING THE AGENTS

TECHNICAL FIELD

The present invention relates to a *Bacillus* sp. D747 strain and to applications thereof. More particularly, the present invention relates to an agent for controlling a plant disease and/or an agent for controlling an insect pest comprising, as an active bacterium, the *Bacillus* sp. D747 strain exhibiting effects of controlling plant diseases and effects of controlling pests, and relates to a control method using these control agents.

BACKGROUND ART

As examples of methods for controlling plant diseases and pests, mention may be made of physical control methods and field husbandry control methods which employ crop rotation or solar heating, chemical control methods using agrichemicals, control methods utilizing disease-resistant varieties, biological control methods using attenuated viruses or antagonistic microorganisms on pathogenic fungi, and the like. Among these methods, research and development for agrichemicals and particularly organo-synthetic fungicides have been significantly improved in recent years, and many agents having high potency and exhibiting various effects are continuously being developed. Furthermore, various application methods have also been provided. The chemical control methods using these have greatly contributed to controlling plant diseases, saving labor in controlling operations, and the like, and have been widely employed. However, recently, it is observed in some crop plants and diseases that controlling effects provided by chemical control methods are reduced due to the appearance of so-called chemical-resistant pests, and this has become a problem. In addition, as a result of continuous cropping forced by spreading of monocultures, outbreaks of infectious diseases via soil, which are believed to be difficult to control with agrichemicals, have become a serious problem in various locations. Furthermore, in methods in which large amounts of agrichemicals are repeatedly employed, chemical substances, which are not naturally present, are released into the environment. For this reason, it has been understood that not only chemicals which are directly toxic to animals and plants, but also non-toxic chemicals, can cause adverse effects on the environment.

As described above, the control of diseases with agrichemicals is highly likely to reduce controlling effects due to the appearance of resistant pests. In this case, it is necessary to develop new fungicides. In addition, with respect to controlling diseases which are believed to be difficult to control with agrichemicals, alternative means or means used together with other methods must be implemented. In addition, it is desired that a control technique which is safer in view of the environment be established.

Recently, in light of these circumstances, controlling methods depending on the use of agrichemicals are being reconsidered, and biological control methods utilizing microorganisms (so-called biological control agents) which are believed to be safer for the environment compared with agrichemicals have been proposed, and some of these have been put to practical use.

In research for biological control of plant diseases, utilization of attenuated viruses, utilization of attenuated pathogenic or non-pathogenic type microorganisms of pathogenic microbes, utilization of antagonistic microorganisms, and the like, have been attempted. Among these, there is much research on utilization of antagonistic microorganisms. In addition, there are many reports on research for controlling diseases among the antagonistic microorganisms in the genus *Bacillus*. However, the genus *Bacillus* has not been found to exhibit effects for controlling a broad spectrum of diseases.

DISCLOSURE OF THE INVENTION

An object of the present invention is to isolate a novel strain exhibiting effects of controlling diseases of plural varieties of plant diseases and/or controlling insect pests.

Another object of the present invention is to provide an agent for controlling a plant disease and/or an agent for controlling an insect pest, comprising, as an active bacterium, the aforementioned strain, which can be effectively employed as a biological control agent.

Another object of the present invention is to provide a method for controlling plant diseases and/or insect pests using the agent for controlling a plant disease and/or the agent for controlling an insect pest described above.

The present inventors discovered that a novel strain belonging to the genus *Bacillus* isolated from nature exhibits effects of controlling several varieties of plant diseases and exhibits effects of controlling pests without harming plant growth, thus completing the present invention.

The present invention relates to a strain described below, an agent for controlling a plant disease and/or an agent for controlling an insect pest, and a method for controlling plant diseases and/or controlling insect pests.

(1) A *Bacillus* sp. D747 strain.
(2) An agent for controlling a plant disease characterized by comprising the *Bacillus* sp. D747 strain as an active bacterium.
(3) An agent for controlling an insect pest characterized by comprising the *Bacillus* sp. D747 strain as an active bacterium.
(4) A method for controlling a plant disease and/or an insect pest characterized by employing the agent for controlling a plant disease described in (2) above and/or the agent for controlling an insect pest described in (3) above.

[Isolation of the *Bacillus* sp. D747 Strain and Deposition Thereof]

The *Bacillus* sp. D747 strain of the present invention is a strain isolated from the air in Kikugawa-cho, Ogasa-gun, Shizuoka-ken, JAPAN. As a result of identification of the strain in view of the bacterial characteristics described below in accordance with *Bergey's Manual of Systematic Bacteriology*, Volume 1 (1984), it was believed that it was a novel strain belonging to the genus *Bacillus*, and might be a *Bacillus cereus*. For this reason, the strain was deposited as "*Bacillus cereus* D747" at the Agency of Industrial Science and Technology, National Institute of Bioscience and Human Technology, on Nov. 28, 2000.

However, after that, it was again studied in detail as to whether or not it belonged to *Bacillus cereus*. As a result, the study provided only the confirmation that it belonged to the genus *Bacillus*. For this reason, a notification of change of the name of the strain to "*Bacillus* sp. D747" was submitted on Apr. 1, 2002.

Therefore, the *Bacillus* sp. D747 strain (hereinafter, simply referred to as the "D747 strain") according to the present invention was deposited at the National Institute of Advanced Industrial Science and Technology, International Patent Organism Depositary as "*Bacillus* sp. D747" with Accession Number "FERM P-18128", and was then transferred to be deposited under the Budapest Treaty on Nov. 8, 2002, as "*Bacillus* sp. D747" with new Accession Number "FERM BP-8234".

[Bacterial Characteristics of the D747 Strain]

The bacterial characteristics of the D747 strain according to the present invention are described as follows. The tests for the bacterial characteristics were carried out in accordance with *Bergey's Manual of Systematic Bacteriology* mentioned above.

(A) Morphological Characteristics
Morphology: *bacillus*
Size: width=1.0 to 1.2 μm; length=3 to 5 μm
Mobility: +
Flagellar adherent condition: periphery flagella
Endospore: +
Spore position: center
Spore swelling: –
(B) Cultural Characteristics
Color of colony: white to pale brown
Culturing in a bouillon agar plate medium: A white to cream colored colony is formed, and the surface thereof is wrinkled.
(C) Physiological Characteristics
Gram's stain stainability: +
Nitrate reduction: +
MR test: –
VP test: +
Indole formation: –
Starch hydrolysis: +
Citric acid assimilating ability: +
Inorganic nitrogen source: +
Oxidase: –
Calatase: +
Growth pH 6.8, bouillon medium: +
Growth pH 5.7, bouillon medium: +
Growth temperature, 30° C.: +
Growth temperature, 50° C.: –
Growth NaCl concentration, 2%: +
Growth NaCl concentration, 5%: +
Growth NaCl concentration, 7%: +
Aerobic growth: +
Anaerobic growth: –
O-F test: O
York reaction: –
Acid formation from glucose: +
Acid formation from mannitol: –
Acid formation from L-arabinose: –
Acid formation from D-xylose: –
Gas formation from glucose: –
β-galactosidase: –
NaCl and KCl requiring property: –

[Culturing of the D747 Strain]

In the culturing method of the D747 strain employed in the present invention, the kinds of media, culturing conditions, and the like, can be appropriately selected. As examples of media, mention may be made of, for example, a medium including glucose, peptone, and a yeast extract, and the like, in addition to a common medium such as a bouillon medium. In addition, solid media such as a slant medium, a plate medium, and the like, including agar, in addition to a liquid medium, may be employed. By culturing, the D747 strain multiplies, so that a desirable amount of the strain can be obtained.

As a carbon source of the medium, all materials into which the aforementioned strain can assimilate may be utilized. As examples thereof, mention may be made of various synthetic or natural carbon sources which the D747 strain can utilize, in addition to sugars such as glucose, galactose, lactose, sucrose, maltose, a malt extract, and a starch hydrolysate.

As a nitrogen source of the medium, organic nitrogen-containing products such as peptone, bouillon, yeast extract, and the like, and various synthetic or natural products which the D747 strain is capable of utilizing can be utilized.

In accordance with common methods for culturing microorganisms, inorganic salts such as sodium chloride, phosphates, or the like; salts of a metal such as calcium, magnesium, iron, or the like; micronutrient sources such as vitamins, amino acids, or the like; can be added, if necessary.

Culturing can be carried out under aerobic conditions such as shake culturing, aeration culturing, or the like. The culturing temperature ranges from 20 to 30° C., and preferably ranges from 25 to 30° C.; the pH ranges from 5 to 8, and preferably ranges from 6 to 7; and the culturing period suitably ranges from 1 to 4 days, and preferably ranges from 2 to 3 days.

The *Bacillus* sp. D747 strain according to the present invention exhibits properties of controlling various plant diseases and controlling pests by administering cultures thereof (including the bacteria per se) or treated products thereof (a mixture of a culture and other ingredients, or the like), or bacteria isolated by culturing (bacteria obtained by treating a culture by centrifugation, or cleansed bacteria thereof, or the like) or treated products thereof (a mixture of the isolated bacteria and other ingredients, or the like), or treated products of those described above (a diluted product thereof with a liquid or a solid, or the like), on the plant parts such as roots, stems, leaves, seeds, and the like, or in the culture soil.

The D747 strain of the present invention can control plant diseases caused by bacteria and fungi belonging to genera *Oomycetes, Ascomycetes, Basidiomycetes*, and *Deuteromycetes*.

As examples of pest fungi causing diseases which the D747 strain can control, mention may be made of, for example, *Pseudoperonospora* such as *Pseudoperonospora cubensis, Venturia* such as *Venturia inaequalis, Erysiphe* such as *Erysiphe graminis, Pyricularia* such as *Pyricularia oryzae, Botrytis* such as *Botrytis cinerea, Rhizoctonia* such as *Rhizoctonia solani, Puccinia* such as *Puccinia recondite, Septoria* such as *Septoria nodorum, Sclerotinia* such as *Sclerotinia sclerotiorum, Pythium* such as *Pythium debaryanum Hesse*; as bacteria, *Burkholderia* such as *Burkholderia plantarii*; and the like. It should be understood that they are not limited to these examples in the present invention.

In addition, the D747 strain of the present invention can control pests such as hemipterous pests, lepidopterous pests, coleopterous pests, dipterous pests, orthopteran pests, isopterous pests, thysanopterous pests, tetranychidaeous pests, and the like.

As examples of pests which the D747 strain can control, mention may be made of, for example, hemipterous pests including Pentatomidae (*Heteroptera*) such as *Riptortus clavatus* and the like, Cicadellidae such as *Nephotettix cincticeps* and the like, Delphacidae such as *Nilaparvata lugens* and the like, Psyliidae such as *Psylla* sp., and the like, Aleyrodidae such as *Bemisia tabaci* and the like, Aphididae such as *Myzus persicae* and the like, Pseudococcoidae such as *Pseudococcus comstocki* and the like; lepidopterous pests including Torticoidea such as *Homona Magnanima* and the like, Cochylidae such as *Eupoecillia ambiguella* and the like, Psychidae such as *Bambalina* sp., and the like, Gracillariidae such as *Nemapogon granellus* and the like, Phyllocnistinae such as *Phyllocnistis citrella* and the like, Yponomeutidae such as *Plutella xylostella* and the like, Pyralidae such as *Chilo suppressalis* and the like, Noctuidae such as *Heliothis virescens* and the like; coleopterous pests including Scarabaeidae such as *Anomala cuprea* and the like, Coccinellidae such as *Epilachna vigintioctopunctata* and the like, Curculionidae such as *Lissorhoptrus oryzophilus* and the like; dipterous pests such as *Culex pipiens, Anopheles sinensis, Culex tritaeniorhynchus*, and the like; orthopteran pests such as *Blatella germanica*, and the like; isopterous pests such as *Reticulitermes speratus*, and the like; thysanopterous pests such as *Scirtothrips dorsali*, and the like; tetranychidaeous pests such as *Tetranychus urticae*, and the like; other harmful animals, creatures to be repelled, insect pests in view of sanitation, parasites, examples of which include Gastropoda such as *Pomacea canaliculat, Incilaria* sp., and the like; and Isopoda such as *Armadillidium* sp., and the like. It should be understood that the present invention is not limited to these examples.

Agents for Controlling Plant Diseases and Agents for Controlling Pests

The agents for controlling plant diseases and agents for controlling pests according to the present invention comprise, as an active bacterium, the D747 strain which can control plant diseases and insect pests as described above. In the agents for controlling plant diseases and agents for controlling pests of the present invention, the D747 strain can be employed alone or in combination with a variant of the D747 strain. The variants have the bacterial characteristics of the D747 strain described above, exhibit effects of controlling plant diseases, and exhibit effects of controlling pests. Spontaneous mutant strains, mutant strains produced by using UV rays or chemical mutagen agents, cell fusion strains, and genetic recombination strains can be utilized therefor. In the present invention, the D747 strain contained in the agents for controlling plant diseases and the agents for controlling pests also include the variants of the D747 strain.

The term "controlling" in the specification is used to mean not only preventing and repelling diseases or pests, but also removing and destroying them. Therefore, even for plants which have been infected by pathogenic fungi, if the agents for controlling plant diseases are applied thereto, the pathogenic fungi can be removed from the plants, and thereby, pathogeny caused by the pathogenic fungi and deterioration of the diseases can be prevented. In addition, pests can also be controlled due to the effects of repelling and killing pests.

For the case in which the D747 strain is included as viable microorganisms in the agents for controlling plant diseases and the agents for controlling insect pests according to the present invention, it is preferable that the strain be applied to the plant body at a concentration ranging from $10^5$ to $10^{10}$ microorganisms/ml.

In addition, for the case in which a culture of the D747 strain is employed, the application timing and the application quantity thereof may be appropriately determined in accordance with the case of the viable microorganisms described above.

In addition, in the agents for controlling plant diseases and the agents for controlling insect pests according to the present invention, the D747 strain may be employed alone as the strain, or a culture thereof may be employed, as formulations in which the strain is diluted with an inert liquid or solid carrier, and surfactants and other auxiliary agents are added thereto, if necessary. As examples of formulations, mention may be made of granules, fine powders, wettable powders, suspensions, emulsifiable concentrates, and the like. As examples of preferable carriers, mention may be made of porous solid carriers such as talc, bentonite, clay, kaolin, diatomaceous earth, white carbon, vermiculite, slaked lime, siliceous sand, ammonium sulfate, and urea; liquid carriers such as water, isopropyl alcohol, xylene, cyclohexanone, methylnaphthalene, and alkyl glycol; and the like. As examples of surfactants and dispersants, mention may be made of, for example, dinaphthylmethanesulfonates, alcohol sulfates, alkyl aryl sulfonates, lignin sulfonates, polyoxyethylene glycol ethers, polyoxyethylene alkyl aryl ethers, polyoxyethylene sorbitan monoalkylates, and the like. As examples of auxiliary agents, mention may be made of carboxymethylcellulose, polyethylene glycol, propylene glycol, gum arabic, xanthan gum, and the like. As examples of protective agents, mention may be made of skim milk, pH buffers, and the like. In this case, the amount of the viable microorganisms of the D747 strain and/or the amount of the cultures thereof, the application timing, and the application quantity can be appropriately determined in accordance with the case of the viable microorganisms described above.

Furthermore, the agents for controlling plant diseases and the agents for controlling pests according to the present invention may include other ingredients such as pesticides, other fungicides, herbicides, plant growth modifiers, fertilizers and manures, and the like, as active ingredients, if necessary. In addition, the agents for controlling plant diseases and the agents for controlling insect pests according to the present invention may include different varieties of strains from the D747 strain, together with the D747 strain.

The agents for controlling plant diseases and the agents for controlling insect pests according to the present invention can be directly applied or can be applied after diluting the agents with water or the like. The methods for applying the agents for controlling plant diseases and the agents for controlling insect pests are not particularly limited. As examples thereof, mention may be made of, for example, a method in which they are directly sprayed to plants or insect pests, a method in which they are sprayed on soil, a method in which they are added to water or fertilizers and manures to be applied to the plants or soil, and the like. In addition, the amount of applied formulations will vary depending on the diseases to be controlled, insect pests to be controlled, plants to which they are to be applied, application methods, the nature of occurrence of the diseases or pests, the degree of damage, environmental conditions, the forms of formulations to be used, and the like. For this reason, it is preferable that the amount of the applied formulations be appropriately adjusted.

As described above, the *Bacillus* sp. D747 strain of the present invention controls a wide spectrum of diseases and pests, and can control multiple varieties of plant diseases and pests.

The agents for controlling plant diseases and the agents for controlling pests comprising the D747 strain according to the present invention can control plant diseases and pests. For this reason, they can be employed as biological control agents. Therefore, the agents for controlling plant diseases and the agents for controlling insect pests of the present invention are highly safe with respect to the environment, and exhibit effects of controlling multiple varieties of diseases and pests. For this reason, they can widely prevent diseases and pests without employing other means for simultaneous use therewith.

BEST MODES FOR CARRYING OUT THE INVENTION

The present invention is described in detail be means of the Examples described below. However, it should be understood that the present invention is not limited to these Examples.

EXAMPLE 1

Culturing of the D747 Strain

The D747 strain was isolated from the air in Kikugawa-cho, Ogasa-gun, Shizuoka-ken, JAPAN. More particularly, in order to isolate the microorganisms present in the air at Kamo, Kikugawa-cho, Ogasa-gun, Shizuoka-ken, JAPAN, a plate medium containing a potato-dextrose agar was allowed to stand for 10 minutes with the lid off so as to be in contact with the air. The medium was incubated for 3 days at 27° C., and the formed colony was isolated. The isolated colony was incubated with a shaker in a medium of a potato-dextrose liquid. The strain exhibiting activities with respect to plant diseases was discovered, thus resulting in isolation of the D747 strain.

The isolated D747 strain was incubated at 27° C. on a rotary shaker at 120 rpm for 3 days in a medium having a pH of 6.0 and comprising 1% of glucose, 2% of a soluble starch, 0.5% of polypeptone, 1% of a dry yeast, 1% of defatted soybeans, 0.2% of $KH_2PO_4$, 0.2% of NaCl, and 0.3% of calcium carbonate. Subsequently, the strains were collected by centrifugation (10,000×g, for 15 minutes), were suspended in sterilized water, and were washed to remove the medium ingredients. The serial procedures described above were repeated twice. Subsequently, the strains were again suspended in sterilized water at a concentration of approximately $10^9$/ml.

EXAMPLE 2

Test on the Effects of Controlling Infection by Rice Blast

Rice seeds (variety: Aichi Asahi) were sown at a rate of 10 grains each in clay pots having a diameter of 7.5 cm, and were allowed to grow in a greenhouse. A suspension of the D747 strains produced as described in Example 1 was sprayed at a rate of 10 ml per pot on the rice seedlings at their 4-leaf stage. After being dried in the air, the seedlings were inoculated by spraying a spore suspension of rice blast (*Pyricularia oryzae*) fungi, and were placed in a moist chamber. On the fifth day after the inoculation, the number of lesions on the fourth leaf was counted, and was evaluated as the extent of lesions on the basis of the evaluation criteria shown in Table 1 described below. The test results are shown in Table 2.

TABLE 1

| Evaluation | |
|---|---|
| A | No lesions were observed. |
| B | Less than 20% based on the extent of lesions in the untreated plot |

TABLE 1-continued

| Evaluation | |
|---|---|
| C | 20% or more but less than 50% based on the extent of lesions in the untreated plot |
| D | 50% or more based on the extent of lesions in the untreated plot |

EXAMPLE 3

Test on the Effects of Controlling Infection by Rice Sheath Blight

Rice seeds (variety: Kinmaze) were sown at a rate of 10 grains each in clay pots having a diameter of 6.0 cm, and were allowed to grow in a greenhouse. A suspension of the D747 strains produced as described in Example 1 was sprayed at a rate of 10 ml per pot on the rice seedlings at their 2-through 3-leaf stages. After being dried in the air, the seedlings were inoculated with rice sheath blight (*Thanatephorus cucumeris*) fungi, and were placed in a moist chamber. On the fifth day after the inoculation, the heights of lesions were measured, and were employed as an evaluation of the extent of lesions. Evaluation was carried out on the basis of the evaluation criteria shown in Table 1 described above. The test results are shown in Table 2.

EXAMPLE 4

Test on the Effects of Controlling Infection by Wheat Glume Blotch

Wheat seeds (variety: Nourin No. 61) were sown at a rate of 10 grains each in plastic pots having a diameter of 6.0 cm, and were allowed to grow in a greenhouse. A suspension of the D747 strains produced as described in Example 1 was sprayed at a rate of 10 ml per pot on the wheat seedlings at their 2-leaf stage. After being dried in the air, the seedlings were inoculated with pycnospores of wheat glume blotch (*Septoria nodorum*) fungi, and were placed in a greenhouse. On the tenth day after the inoculation, the infected area of the first leaf in each pot was measured, and was employed as an evaluation of the extent of lesions. Evaluation was carried out on the basis of the evaluation criteria shown in Table 1 described above. The test results are shown in Table 2.

EXAMPLE 5

Test on the Effects of Controlling Infection by Wheat Powdery Mildew

Wheat seeds (variety: Nourin No. 61) were sown at a rate of 10 grains each in plastic pots having a diameter of 6.0 cm, and were allowed to grow in a greenhouse. A suspension of the D747 strains produced as described in Example 1 was sprayed at a rate of 10 ml per pot on the wheat seedlings at their 1.5- through 2-leaf stages. After being dried in the air, the seedlings were inoculated with conidiospores of wheat powdery mildew (*Erysiphe graminis*), and were placed on a bench in a greenhouse until an infection measurement was carried out. On the tenth day after the inoculation, the infected area of the first leaf in each pot was measured, and was employed as the extent of lesions. Evaluation was carried out on the basis of the evaluation criteria shown in Table 1 described above. The test results are shown in Table 2.

EXAMPLE 6

Test on the Effects of Controlling Infection by Cucumber Gray Mold

Cucumber seeds (variety: Sagami Hanjiiro) were sown at a rate of 4 grains each in plastic pots having a diameter of 6.0 cm, and were allowed to grow in a greenhouse. A suspension of the D747 strains produced as described in Example 1 was sprayed at a rate of 10 ml per pot on the young cucumber seedlings in their cotyledonous stage. After being dried in the air, the seedlings were inoculated by placing a paper disk which was immersed in a spore suspension of cucumber gray mold (*Botrytis cinerea*) fungi on the surface of the cotyledons of the cucumber seedlings, and were subsequently placed in a moist chamber at 20° C. On the third day after the inoculation, the infected area of the cotyledons was measured, and was employed as an evaluation of the extent of lesions. Evaluation was carried out on the basis of the evaluation criteria shown in Table 1 described above. The test results are shown in Table 2.

EXAMPLE 7

Test on the Effects of Controlling Infection by Cucumber Downy Mildew

Cucumber seeds (variety: Sagami Hanjiiro) were sown at a rate of 4 grains each in plastic pots having a diameter of 6.0 cm, and were allowed to grow in a greenhouse. A suspension of the D747 strains produced as described in Example 1 was sprayed at a rate of 10 ml per pot on the young cucumber seedlings in their cotyledonous stage. After being dried in the air, the seedlings were inoculated by spraying a zoosporangium suspension of cucumber downy mildew (*Pseudoperonospora cubensis*) fungi, and were subsequently allowed to stand in a moist chamber at 22° C. for 24 hours. On the eighth day after the inoculation, the infected area of the cotyledons was measured, and was employed as an evaluation of the extent of lesions. Evaluation was carried out on the basis of the evaluation criteria shown in Table 1 described above. The test results are shown in Table 2.

TABLE 2

| Example No. | Plant disease tested | Controlling effect by the D747 strain |
| --- | --- | --- |
| 2 | rice blast | A |
| 3 | rice sheath blight | A |
| 4 | wheat glume blotch | A |
| 5 | wheat powdery mildew | A |
| 6 | cucumber gray mold | A |
| 7 | cucumber downy mildew | A |

EXAMPLE 8

Mortality Test of *Lissorhoptrus oryzophilus*

A suspension of the D747 strain produced as described in example 1, in an amount of 30 ml, was placed in a plastic cup having a volume of 60 ml. Three pieces of rice leaves having a length of 3 cm were floated thereon. Ten imagoes of *Lissorhoptrus oryzophilus* were released therein, and the cup was closed with a cover. After it was allowed to stand in a thermostatic chamber at 25° C. for 3 days, the number of living pests was counted. The test was carried out three times. A mortality rate was calculated by equation (1) described below. A definitive mortality rate was determined by calculating an average value of the three values. The test results are shown in Table 3.

Mortality rate(%)={[10−(the number of living pests)]/10}× 100

TABLE 3

| | Definitive mortality rate (%) |
| --- | --- |
| Treated with the D747 strain | 100 |
| No treatments | 0 |

As is apparent from the results shown in Table 2 and Table 3, the plants to which the agents for controlling plant diseases and the agents for controlling insect pests comprising the D747 strain according to the present invention were applied exhibited superior controlling effects with respect to various plant diseases and pests.

INDUSTRIAL APPLICABILITY

The present invention has characteristics in that a novel strain of *Bacillus* sp. D747 (FERM BP-8234) was discovered. By administering cultures of the *Bacillus* sp. D747 strain (including the viable bacteria) or viable bacteria isolated by culturing, on plant parts such as roots, stems, leaves, seeds, and the like, or in the culture soil, outbreaks of various plant diseases in an extremely wide range can be controlled, and pests can be controlled. In addition, the plants on which the agents for controlling plant diseases and the agents for controlling insect pests comprising the D747 strain according to the present invention are sprayed can exhibit superior controlling effects with respect to various plant diseases and pests.

The invention claimed is:

1. A biologically pure bacterial isolate having all the identifying characteristics of *Bacillus* sp. D747, deposited under FERM BP-8234.

2. A composition comprising the isolate of claim 1 as an active bacterium and one or more liquid or solid carrier(s).

3. The composition of claim 2 which comprises $10^5$ to $10^{10}$ bacteria of said isolate per mL of said composition.

4. The composition of claim 2 which is a granule, fine powder or wettable powder.

5. The composition of claim 2 which is a suspension or emulsifiable concentrate.

6. The composition of claim 2 which is a solid, and wherein said solid carrier comprises a porous solid carrier.

7. The composition of claim 2 which is a liquid and comprises a liquid carrier.

8. The composition of claim 2, further comprising one or more liquid carriers selected from the group consisting of water, isopropyl alcohol, xylene, cyclohexanone, methylnaphthalene, and alkyl glycol.

9. The composition of claim 2, further comprising a surfactant or dispersant.

10. The composition of claim 2, further comprising at least one pesticide or fungicide.

11. The composition of claim 2, further comprising at least one herbicide.

12. The composition of claim 2, further comprising at least one plant growth modifier, fertilizer or manure.

13. A method for treating a fungal disease in a plant comprising contacting said plant with a composition comprising a biologically pure bacterial isolate having all the identifying characteristics of *Bacillus* sp. D747, deposited under FERM BP-8234.

14. The method of claim 13, wherein said plant is rice and the fungal disease is caused by rice blast fungus, *Pyricularia oryzae*.

15. The method of claim 13, wherein said plant is rice and the fungal disease is rice sheath blight caused by *Thanatephorus cucumeris*.

16. The method of claim 13, wherein said plant is wheat and the fungal disease is wheat glume blotch caused by *Septoria nodorum*.

17. The method of claim 13, wherein said plant is wheat and the fungal disease is wheat powdery mildew, *Erysiphe graminis*.

18. The method of claim 13, wherein said plant is cucumber and the fungus is cucumber gray mold, *Botrytis cinerea*.

19. The method of claim 13, wherein said plant is cucumber and said fungus is cucumber downy mildew, *Pseudoperonospora cubensis*.

20. A method for treating a plant infested with an insect pest, wherein said plant is rice and said in sect pest is *Lissorhoptus oryzophilus*.

21. A method for making a composition, comprising culturing the bacterial isolate of claim 1, recovering said bacterial isolate, and admixing said bacterial isolate with a solid or liquid carrier.

* * * * *